United States Patent [19]

Brajnovic

[11] Patent Number: 4,872,839
[45] Date of Patent: Oct. 10, 1989

[54] SPACER FOR DENTAL IMPLANTS

[75] Inventor: Izidor Brajnovic, Gothenburg, Sweden

[73] Assignee: Nobelpharma AB, Gothenburg, Sweden

[21] Appl. No.: 195,334

[22] Filed: May 18, 1988

[30] Foreign Application Priority Data

Jun. 12, 1987 [SE] Sweden .................................. 8702445

[51] Int. Cl.⁴ ................................................ A61C 8/00
[52] U.S. Cl. ...................................... 433/173; 433/174
[58] Field of Search ................................. 433/173, 174

[56] References Cited

U.S. PATENT DOCUMENTS 4,657,510 2/1987 Gittleman ........................... 433/173
4,756,689 7/1988 Lundgren ........................... 433/173

FOREIGN PATENT DOCUMENTS 0125203 4/1984 European Pat. Off. .
0180247 7/1986 European Pat. Off. .
1067975 10/1959 Fed. Rep. of Germany .

Primary Examiner—Robert Peshock
Attorney, Agent, or Firm—Pollock, Vande Sande & Priddy

[57] ABSTRACT

A spacer for dental implants of a bio-compatible material includes an inner sleeve-shaped spacer element of titanium which is part of a screw connection between an anchorage element implanted in the maxillary beneath the gingiva, and a dental prosthesis construction whose joint surface is located above the gingiva and which is disposed to absorb the loading of the screw connection. The spacer includes an outer spacer sleeve of porcelain or ceramics which wholly or partly encloses the inner sleeve-shaped spacer element. The ceramic or porcelain sleeve may, by grinding and coating with porcelain of different colors, be caused to visually approximate a dental cervix and gingiva and, thereby, not contrast with the natural dental cervix color and gingival color.

6 Claims, 1 Drawing Sheet

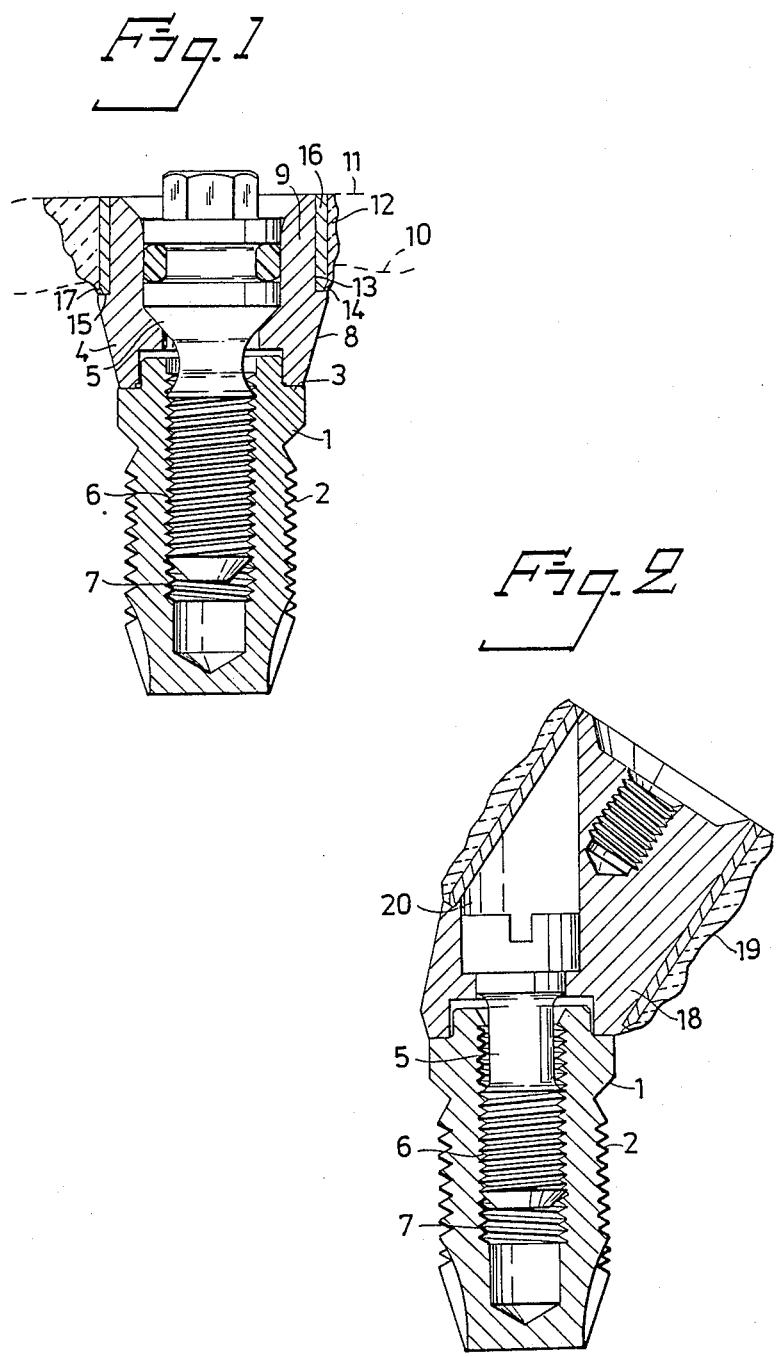

SPACER FOR DENTAL IMPLANTS

BACKGROUND OF THE INVENTION

1. Technical Field

The present invention relates to a spacer for dental implants of a bio-compatible material and constituting a connection element in a removable screw connection between an anchorage (fixture) implanted in the maxillary beneath the gingiva, and a dental prosthesis construction whose joint surface is located above the gingiva.

2. Background Art

It is previously known in this art to permanently anchor all prostheses in the maxillary by means of helicoid anchorage elements, so-called fixtures, of a bio-compatible material, preferably pure titanium. The method which has displayed the highest degree of anchorage stability and which has successfully been used clinically for more than 20 years is the so-called osseointegration method developed by professor Per-Ingvar Brånemark et al and described in, for example, Brånemark/Zarb/Albrektsson: "Tissue-Integrated Prostheses", Quintessence Books, 1985.

The method is based on a highly exact and atraumatic implant technique of the fixture such that a direct contact, in other words an exact adaptation without interjacent soft tissue, occurs between the fixture and the bone tissue. Such a direct contact between fixture and bone tissue provides the best preconditions for a really permanent fixation of, for example, a dental prosthesis.

The helicoid fixtures of pure titanium are implanted into the maxillary in a first surgical operation which is followed by an unloaded healing phase of critical length during which time the fixture is covered by intact mucous membrane. During this healing phase, the bone tissue grows onto and forms a unit with the implanted fixture. In a second operation, the fixture is then exposed and a substantially tubular spacer is applied to the fixture by means of a spacer screw. Subsequently, the dental prosthesis proper, in the form of a bridge construction, is united to the fixture by means of a fixing screw which, in its turn, anchors in the spacer screw.

A bridge construction is anchored in place by means of a plurality of fixtures, for example six in number, and corresponding spacers which constitute connection elements between the bridge construction and the fixtures. To be able to absorb the extreme oral loadings to which the screw connection is subjected, the spacers are of a bio-compatible material of extremely good strength properties, for example titanium or the like.

Normally, the connection portion (base portion) of the spacer against the fixture will, after the operation, be enclosed by the gingiva. However, the major portion of the spacer will project up above the edge of the gingiva in that gap which is formed between the gingival edge and the joint surface of the bridge construction. Normally, such exposure of the spacer will seldom constitute an inconvenience, since the spacer is concealed behind the patient's lips. However, in certain cases when the lips are raised considerably, the spacers will also become visible during speech and normal mimicry, a factor which may be disadvantageous for esthetic reasons, because of the visible contrast of the metal surface of the spacers against the surrounding dental cervix and gingival color of the patient.

Even in those cases where such spaces are very seldom exposed to view, it may be psychologically disturbing for the patient. It is not possible to design the bridge construction in such a manner that it descends to the gingival edge and masks the spacers, since there must be a sufficiently wide gap or space between the gingival edge and the joint surface of the bridge construction about the spacer in order to make possible cleaning in the interface zone between the implant material and the gingival tissue. Such cleaning is of vital importance to prevent occurrence of gingivitis, which may spread in the interface zone between the implant material and the bone tissue and jeopardize the anchorage of the dental implant.

SUMMARY OF THE INVENTION

The object of the present invention is to solve the above-outlined problems and design the spacer in such a manner that it will be less visually dominant in those cases when it is exposed to view. The present invention constitutes a solution to these problems.

BRIEF DESCRIPTION OF THE ACCOMPANYING DRAWINGS

The nature of the present invention and its aspects will be more readily understood from the following brief description of the accompanying drawings, and discussion relating thereto.

In the accompanying drawings:

FIG. 1 is a section through a first embodiment of the present invention; and

FIG. 2 shows an alternative embodiment in conjunction with an angled spacer.

DESCRIPTION OF PREFERRED EMBODIMENT

Referring to the Drawings, FIG. 1 shows an anchorage element in the form of a cylindrical screw 1 of titanium with an exterior thread 2 intended to be inserted in a predrilled hole in the maxillary for permanent anchorage of a dental prosthesis. A spacer has been connected to the upper portion 3 of the fixture, the spacer comprising a substantially tubular spacer element 4 also of titanium, and a spacer screw 5 provided with a threaded portion 6 which engages with an interiorally threaded bore 7 in the upper region of the fixture for fixedly anchoring the spacer 4 to the fixture.

Both the fixture and the spacer screw are of known design and will not, therefore, be described in greater detail here. Both consist of standard components included in Nobelpharma Implant System. However, the spacer has been modified as compared with prior art spacer members.

The spacer element 4 is provided with a lower, substantially conically tapering portion 8 for gingival penetration, and an upper cylindrical portion 9 which projects above the gingival edge 10 and extends from the above-mentioned conical portion up to the joint surface 11 of a prosthesis construction (dental bridge), not shown. The spacer element 4 is of pure titanium, which is of documented bio-compatibility and possesses moreover good strength properties, enabling it to absorb the forces of the screw connection.

Depending upon the conditions prevailing in the mouth, the cylindrical portion of the spacer element will, after mounting of the prosthesis construction, normally be exposed. As was mentioned by way of introduction, such exposure is also normal so as to permit cleaning about the spacer members. However, because the titanium in the spacer element is in stark contrast to the dental cervix color and gingival color, this may be esthetically disturbing to certain patients. Consequently, according to the present invention, at least the cylindrical portion of the spacer element 4 is provided with a coating of a tooth-like material, preferably ceramic or porcelain. This coating is designed as a sleeve 12 which may be loose and solely anchored to the spacer element 4 by a light clamping between prosthesis and spacer element. Because of the frangibility of such materials, the sleeve should not be subjected to any loading. Alternatively, the sleeve may be fused directly to the titanium in the spacer element.

The sleeve 12 of ceramics or porcelain may be ground and coated with porcelain of different colors at a dental technological laboratory for individual detail adaptation to the prevailing situation in the mouth of the patient. Sealing of the microscopic gaps in the joints between the sleeve 12 and the spacer element 4 may be effected using known bio-adapted jointing materials. In those cases where the sleeve is removable, the advantage will be gained that the tissue-sensitive spacer element will not be contaminated or otherwise negatively influenced during the dental technological process.

The spacer element 4 is preferably provided with a milled recess 13 for the spacer sleeve 12, the outer contour 14 of the porcelain/ceramics at the shoulder 15 in the milled recess being adapted to the outer contour of the spacer element.

As has been mentioned above, the spacer sleeve 12 may be loosely adapted to the spacer element 4 or be fused directly to the titanium therein. However, the porcelain/ceramics in the spacer sleeve is preferably disposed on a thin cylinder 16 of gold, aluminium oxide or similar material, as is apparent from both FIGS. 1 and 2. When necessary, a bevelling 17 is effected to the cylinder 16 at the connection to the shoulder 15 in the spacer element, such that the porcelain/ceramics connects directly to the titanium in the surface layer of the spacer element.

FIG. 2 shows an example of an angled spacer element 18 with an external coating in the form of a spacer sleeve 19 of a type similar to that already described with reference to FIG. 1. In this case, the spacer sleeve 19 simultaneously constitutes a sealing against the screw passage 20 in the spacer element 18.

By designing the spacer element in the manner described above, the tissue in the innermost, most critical zone, will be contiguous with the titanium in the spacer element 4, while the sleeve 12 will be contiguous with the other portion of the soft tissue and cover that portion of the spacer element 4 which projects above the gingival edge. The forces of the screw connection are absorbed by the spacer element 4, and connection of the dental prosthesis is effected above the gingival edge, as in existing systems. Hereby, the documented advantages of existing spacer systems will be retained, at the same time as the cosmetically advantageous coating may be inserted without giving rise to any problems of materials strength.

While the present invention is particularly intended for use in conjunction with bridge constructions, it may also be employed in single-tooth restorations. Prior art single-tooth constructions have entailed that the entire dental prosthesis is anchored directly on the fixture beneath the gingiva, which involves problems of adaptation and fit (concealed joint) and disturbances of the healing process of the gingiva against the spacer. According to the present invention, a separate spacer sleeve may be applied on the spacer element and the dental prosthesis proper may be tested and adapted without involving any problems of fit against the concealed joint beneath the gingival edge.

The present invention should not be considered as restricted to that described above and shown on the drawings, many modifications being conceivable without departing from the spirit and scope of the appended claims.

What I claim and desire to secure by Letters Patent is:

1. A spacer for dental implants constituting a connection element in a removable screw connection between an anchorage element implanted in the maxillary beneath the gingiva, and a dental prosthesis construction whose joint surface is disposed above the gingiva, said spacer comprising:

a tubular spacer member made of a bio-compatible material such as titanium for absorbing the loadings of the screw connection;

said tubular spacer element having a lower, substantially conically tapered portion for gingival penetration and an upper cylindrical portion projecting above the gingival edge and extending from said conically tapered portion up to the joint surface of the prosthesis construction;

the outer diameter of the lower end part of said conically tapered portion substantially corresponding to the outer diameter of the upper portion of the anchorage element;

a covering sleeve of a tooth-like material provided substantially around said cylindrical portion of the spacer element; and wherein said covering sleeve is not subjected to any loadings of the screw connection.

2. The spacer as claimed in claim 1, wherein said covering sleeve is made of a porcelain or ceramics.

3. The spacer as claimed in claim 1, wherein said cylindrical portion of said tubular spacer element has an outer milled recess for receiving said covering sleeve, the outer contour of said sleeve at the lower edge of said milled recess following the outer contour of said spacer element.

4. The spacer as claimed in claim 1, wherein said covering sleeve includes an inner cylinder made of gold or aluminum oxide against which a porcelain or ceramics has been applied.

5. The spacer as claimed in claim 1, wherein said spacer element is disposed at an angle with respect to said anchorage element, said covering sleeve constituting a seal against the screw passage in said spacer element.

6. The spacer as claimed in claim 4, wherein said spacer element is disposed at an angle with respect to said anchorage element, said covering sleeve constituting a seal against the screw passage in said spacer element.

* * * * *